(12) United States Patent
Sorensen et al.

(10) Patent No.: US 7,739,125 B2
(45) Date of Patent: Jun. 15, 2010

(54) AUTOMATION OF A DENTAL ENVIRONMENT

(75) Inventors: Kim Sorensen, Klampenborg (DK); Peter Bojsen Sorensen, Charlottenlund (DK)

(73) Assignee: XO Care A/S, Horsholm (DK)

(*) Notice: Subject to any disclaimer, the term of this patent is extended or adjusted under 35 U.S.C. 154(b) by 1310 days.

(21) Appl. No.: 10/548,816

(22) PCT Filed: Mar. 13, 2003

(86) PCT No.: PCT/DK03/00164

§ 371 (c)(1),
(2), (4) Date: Sep. 13, 2005

(87) PCT Pub. No.: WO2004/080324

PCT Pub. Date: Sep. 23, 2004

(65) Prior Publication Data

US 2006/0177795 A1    Aug. 10, 2006

(51) Int. Cl.
*G06Q 10/00* (2006.01)
(52) U.S. Cl. .............................. 705/2; 705/3
(58) Field of Classification Search .................. 433/98, 433/99, 101; 705/2, 3
See application file for complete search history.

(56) References Cited

U.S. PATENT DOCUMENTS

| 4,453,009 A | 6/1984 | Yamaguchi et al. |
| 5,453,009 A * | 9/1995 | Feldman ..................... 433/215 |
| 5,766,228 A * | 6/1998 | Bonnet et al. ................. 607/16 |
| 2004/0059197 A1 * | 3/2004 | Yamashita et al. .......... 600/300 |

FOREIGN PATENT DOCUMENTS

| EP | 0 391 967 B1 | 8/1992 |
| GB | 2 259 162 | 3/1993 |
| WO | WO 94/10931 | 5/1994 |
| WO | WO9827886 | * 7/1998 |
| WO | WO 02/099572 A2 | 12/2002 |

* cited by examiner

*Primary Examiner*—Cris L Rodriguez
*Assistant Examiner*—Sunil K Singh
(74) *Attorney, Agent, or Firm*—Buchanan Ingersoll & Rooney PC (57) ABSTRACT

An information and control system for use in a dental environment has a dental unit with a number of selectable dental instruments and a control member for controlling their operation, a patient's rest and working positions for a dentist and a dental nurse. A computer is provided for storing treatment protocols listing selectable dental treatments, and for each treatment sequential steps to be performed in the treatment. Treatment and actions are displayed, and protocol control means are provided for inputting commands to the computer means for selection of treatments and actions listed in said protocols.

26 Claims, 11 Drawing Sheets

AUTOMATION OF A DENTAL ENVIRONMENT

The invention relates to an information and control system for use in a dental environment, said environment incorporating a dental unit including a number of individually selectable dental instruments, at least one instrument control member for controlling the operation of a selected instrument, a patient's rest and working positions for a dentist and a dental nurse in operative relationship to said dental-unit and said patient's rest, said information and control system comprising computer means storing sequences of treatments for dental conditions and display means for display of a sequence of treatments for a dental condition.

Computerised control of the operation of dental instruments in a dental unit as well as the performance of various auxiliary functions not related to the instrument operation as such is well known in the art. A typical example in the prior art is disclosed in EP-B-0 391 967, which discloses a dental unit including a microprocessor for supervision and control of instrument operation as well as a range of auxiliary functions, whereby instruments and auxiliary functions can be selected by means of a display with associated selection means.

In U.S. Pat. No. 5,453,009 a method and system for dental treatment is disclosed proposing some improvement to the dentist's determination of a sequence of treatments to be used for a specific dental condition by the use of a computer having a memory storing information of all possible dental diseases and problems and possible sequences of treatments for such dental conditions with the aim of avoiding unnecessary or incorrect treatments, without disclosing any information, however, about steps or actions involved in the preparation or a conduct of a treatment.

The object of the present invention is to take the use of information and control technology in a dental environment a step further by providing an information and control system that will significantly improve quality management and control in dental practice by making available to the dentist and/or the dental nurse a range of selectable dental treatments comprising a number of steps or actions giving information during preparation or set-up for a treatment and during the course of the treatment to be performed.

A further object of the invention is to provide a useful improvement of record-keeping in a dental practice by integrating an information and control system with treatments records in a patients register by means of logging capabilities in the information and control system.

A still further object of the invention is to provide a multi-user dental information and control system for shared use by a number of individual dentists in a dental practice.

These and other objects of the invention, as will appear from the following description, are accomplished by an information and control system, which in its general aspect is characterised by computer means storing at least one treatment protocol listing a range of selectable dental treatments, and for each listed treatment a range of sequential steps or actions to be performed in preparation and conduct of the treatment, said computer means being operatively connected or connectible with protocol display means for display of said treatment and actions to the dentist and/or the dental nurse, protocol control means being provided to be operable by the dentist and/or the dental nurse for inputting commands to the computer means for selection of treatments and actions listed in said protocols.

By these provisions, an information and control system is provided, providing the dental personnel with immediate, convenient and efficient access to both overview and details of particular dental treatments as needed or desired, including information on sequential steps and actions in said treatments.

Hereby, the quality and efficiency of a dental practice is improved, and the dentist is relieved of some of his responsibility, which is delegated to the dental nurse. In particular, the information needed by the dental nurse is to a great extent provided by the information and control system, thus facilitating the work of the nurse and relieving the dentist as mentioned.

It is preferred that an information display means is disposed at instrument carrying means at said dental unit, for display of information transferred from said computer means and related to the use of a dental instrument in said dental unit.

Hereby, relevant information related to the use of a particular instrument is presented in an efficient way at a relevant place that is, right next to the instrument to be picked up by the dentist.

In a preferred implementation of the system for use in a dental environment, wherein the dental unit comprises microprocessor means for controlling operational parameters for a selected instrument, the protocol comprises at least one treatment including at least one step or action involving the use of at least one dental instrument in the dental unit, for which a value of at least one operational parameter is stored in said computer means, whereby said computer means may be operatively connected or connectable with said microprocessor means in the dental unit for communication of said parameter value to said microprocessor means and adjustment of said operational parameter to said stored value by selection of said dental instrument.

Hereby, the operational parameters for the selected instrument will be selected correctly by the system, thus relieving the dentist from this task.

The values of said operational parameters are preferably programmable via said computer means.

This feature will enable the dentist to select any particular parameter according to his own skill or experience, for a particular treatment or for a group of treatments.

It is preferred that a parameter display means is disposed at instrument carrying means at said dental unit for display of said parameter value when communicated to said microprocessor means.

Hereby, check of the selected parameters is enabled.

In a preferred embodiment, said information display means and said parameter display means are constituted by one and the same display, thus simplifying the system and improving overview and efficiency.

Said protocol control means comprises preferably many of a keyboard, a point-and-click device, a voice recognition device and/or a separate protocol control member disposed in relationship with said instrument control member.

In an alternative, preferred embodiment, said instrument control member and said separate protocol control member are integrated in a single foot-operated control device.

The functioning of specific controls on said foot-operated control device are preferably programmable via the computer means.

These features provide the dentist with a more detailed control of the information and control system, enabling input of more detailed commands to the system.

For the information of the patient, said protocol display means may preferably comprise a patient's display disposed within a field of vision for the patient while resting in said patient's rest.

In this connection, it is generally preferred that real-time data are displayed on said patient's display related to the treatment, step or action presently performed.

These features will contribute to the comfort of the patient and to a significant degree substitute the conversation between patient and dentist, which is generally impeded by the treatment per se, thereby relieving the dentist and occupying the patient. In addition, a large number of the population are afraid to subject themselves to dental treatment; it is believed that such fear may partly be caused by lack of knowledge on dental procedures.

Said patient's rest is preferably equipped with means such as a cushioning switch for sensing the presence of a patient in the rest.

Hereby, the information of a patient being present may be made available to the computer means and thus, the computer means may register or verify that a treatment is presently being performed.

It is in particular preferred that the computer means comprises logging means for storing logging information, in particular logging information for any selected treatment and any of said sequential actions performed in the course of said treatment.

Said logging means are preferably adapted to logging:

the presence of a patient in the patient's rest; the name of the patient; and the name of the dentist and possible the dental nurse;

the treatments performed, including data such as version number identifying a particular treatment, or possible deviations made during the course of a treatment;

time data related to the treatments performed, such as point of time for start of a treatment, a step or an action, and the duration of same;

time data related to the dental instruments used, such as point of time for start of the use of each instrument and the duration of same, and accumulated periods of use for each instrument;

points of time for the patient entering and leaving, respectively, the patient's rest, as registered by said presence sensing means;

environmental data such as water quality, temperature and/or moisture of air; and bar code data, preferably from bar codes present on items presented to a bar code reader connected to said computer means during a treatment.

These logging provisions enable a computerised logging of the treatment of a patient. From this log, data relevant to the patient may be transferred to the patient's record and stored for documentation of procedures used, dental unit instrument data, materials, used, and preferably in debiting the patient.

Data relevant to dental instruments, such as working hours may be transferred to a record containing information on accumulated working hours for a specific instrument, and data on filling materials used, such as expiry dates, may be transferred to the patient's record. Data related to consumables used, such as product codes and batch numbers may be input via the bar code reader.

Also, registering of whether hand instruments and autoclavable, powered instruments have been autoclaved may be registered via the bar code reader, and a record kept of the autoclaving of each instrument and its subsequent use.

Data relating to the patient, such as personal number, name, address, etc., may be input from an ID card or similar via the bar code reader.

In this connection, it is particularly preferred that the computer means has means preventing deletion of logged data, thereby ensuring the integrity and reliability of the logged data.

In a further development of the dental information and control system, a multi-user system is provided in that the computer means forms part of a multi-user network including a server computer connected with computer means associated with a number of dental units, whereby said treatment protocols are stored in said server computer for shared use by all of said computer means and the dental units associated therewith.

Hereby, several dentists sharing a dental practice will share access to all data common to said practice.

In such a multi-user system the server computer may preferably be adapted for storing of user-defined treatment protocols in addition to said shared protocols.

Hereby, any dentist's personal data will be available in any of the work stations that is, dental environments, connected to the network.

In a particularly preferred further development, the computer means associated with a dental unit and/or said server computer may be adapted for storing a patient's register for patients of a dental practice, said register containing records of treatments and actions performed on each patient therein, said computer means being further adapted for modification of an action listed in said treatment protocol for any of said selectable treatments on the basis of information on prior treatments recorded for the patient in said patient's register.

Hereby, any single treatment performed on a particular patient may be adapted in accordance with circumstances particular to that patient that is, e.g. the amplitude of an ultrasonic scaling device may adapted to a hyper-sensitive patient.

For a specific patient's record, said computer means is preferably adapted for storing information related to the patient such as position adjustment data for the patient's rest.

Hereby, the comfort of the patient is improved, and the patient is imparted a comforting feeling of being welcome and having the dental treatment adapted to his specific needs.

In the following, the invention will be explained in greater detail with reference to the accompanying simplified schematic drawings, in which.

Figure 1:
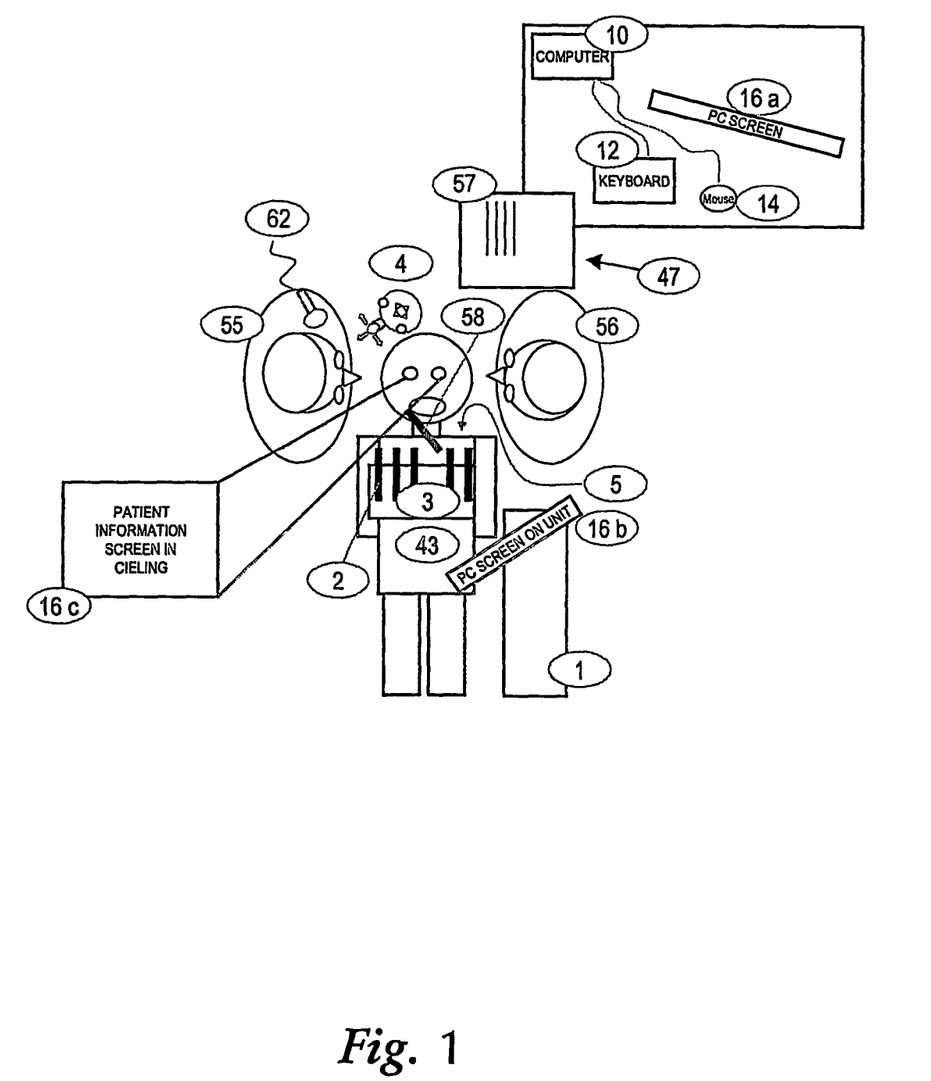
FIG. 1 is a general arrangement of a dental environment incorporating an embodiment of an information and control system according to the invention.

The dental environment illustrated in FIG. 1 comprises a dental unit generally designated by 1. As customary, the dental unit 1 will comprise a number of dental instruments 2 such as different types of motor or air-turbine operated drilling instruments, said instruments being arranged in an instrument carrier 3, as well as a conventional foot-operated switch and control device 4 for operation of an instrument 58, which has been selected by its removal from the instrument carrier 3.

Whereas the dental unit 1 may preferably include a microprocessor for monitoring and controlling operational functions of selected dental instruments 58 as well as auxiliary functions not related to the instrument operation and may in this capacity also include a display 5 for the display of settings or parameters of such operational or auxiliary functions, as known per se from EP-B-0 391 967, this is for the purpose of the present invention an optional feature and the dental unit may as such be of any state-of-the-art configuration.

The instrument carrier 3 with the dental instruments 2 may be disposed on a table-like support, so that a patient's rest 43 schematically illustrated by a resting patient may conveniently be disposed generally below the instrument carrier 3 with its head supporting part positioned shortly outside the table-like support for the instrument carrier 3.

On either side of the head supporting part of the patient's rest 43, working positions 55 and 56 for a dentist and a dental nurse, respectively, are disposed in positions where the dentist as well as the dental nurse will have easy access to the dental instruments as well as other dental equipment and consumables typically positioned in conjunction with either the instrument carrier 3 or a cabinet 57 or the like for hand instruments 47, disposed within reach from the working position of the dental nurse and/or the dentist.

So far described the illustrated dental environment may function as disclosed in the above-mentioned EP-B-0 391 967, the disclosure of which is incorporated herein by reference.

In accordance with the present invention, the dental environment further comprises computer means such as a conventional computer configuration including a processing station 10 with a microprocessor 11, a keyboard 12, a point-and-click device like a mouse 14 and a display screen 16a for use by the dental nurse.

In view of providing an advanced dental information and control system as will be explained in more detail in the following, the illustrated implementation of the computer configuration further comprises an additional display screen 16b disposed in conjunction with the dental unit 1 within the field of vision of the dentist in his working position 55 and the working position 56 of the dental nurse, as well as an information display screen 16c disposed within the field of vision of a patient resting in the patient's rest 43, e.g. secured to the ceiling of the dental clinic room.

Figure 2:
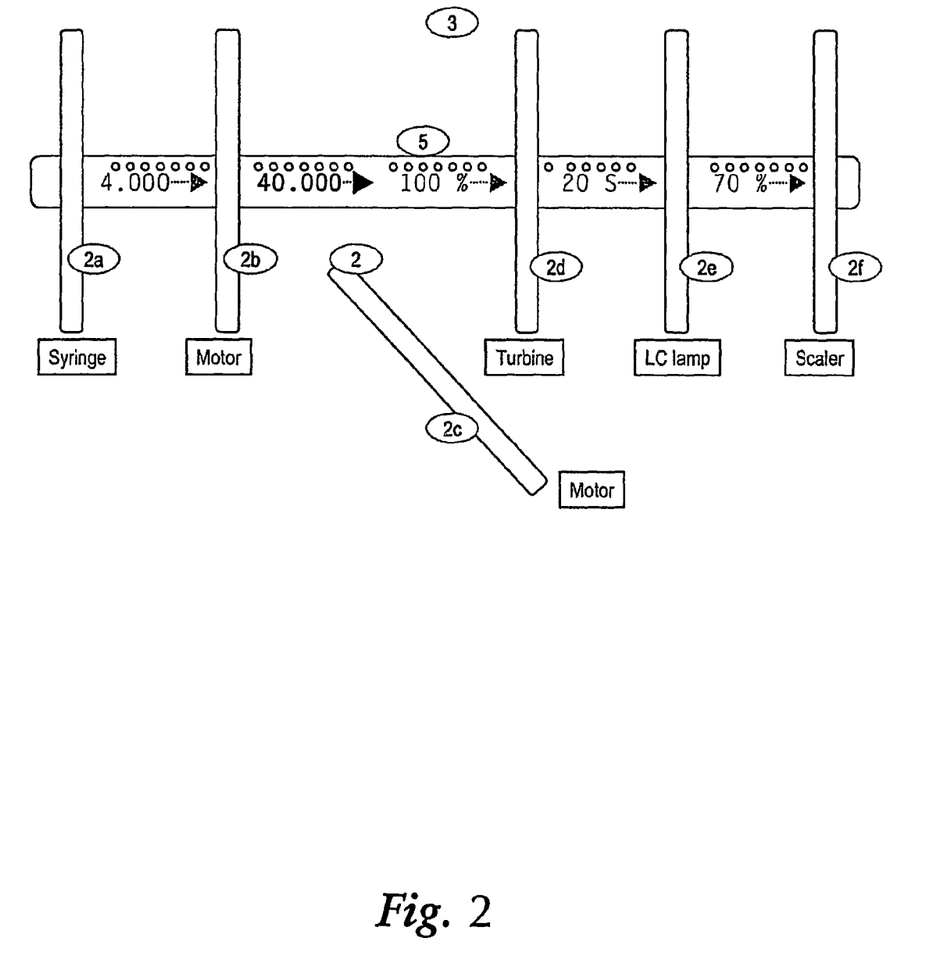
FIG. 2 is a representation of instrument carrying means with an integrated information display forming part of a dental unit in the dental environment shown in FIG. 1.

As illustrated in FIG. 2, the dental instruments 2 arranged in the instrument carrier 3 may conventionally comprise a syringe 2a for applying a water-air coolant and rinsing spray to the dental working area, motor driven drilling instruments 2b and 2c, an air turbine driven drilling instrument 2d, an LC (Light-Curing) lamp 2e for curing of composite filling materials and an ultrasonic scaling instrument 2f. In the illustrated embodiment, the display screen 5 arranged in conjunction with the instrument carrier 3 has a single row of alpha-numeric characters displaying values indicating the current adjustment of operational parameters for the dental instruments as provided by the microprocessor incorporated in the dental unit 1, such as the rotational speed of drilling instruments. Optionally the screen 5 may for each instrument be provided with an array of indicator lamps such as light emitting diodes, one of which may illuminate for a particular setting of an operational parameter to indicate the position of the set value within the total adjustment range of the parameter in question.

In accordance with the invention, an advanced information and control system is provided for the dental environment, by which the computer means as illustrated e.g. by the computer configuration shown in FIG. 1 stores a treatment protocol listing a range of selectable dental treatments and for each of the treatments listed in the protocol a range of sequential steps or actions to be performed in preparation and conduct of the treatment.

Figure 3:
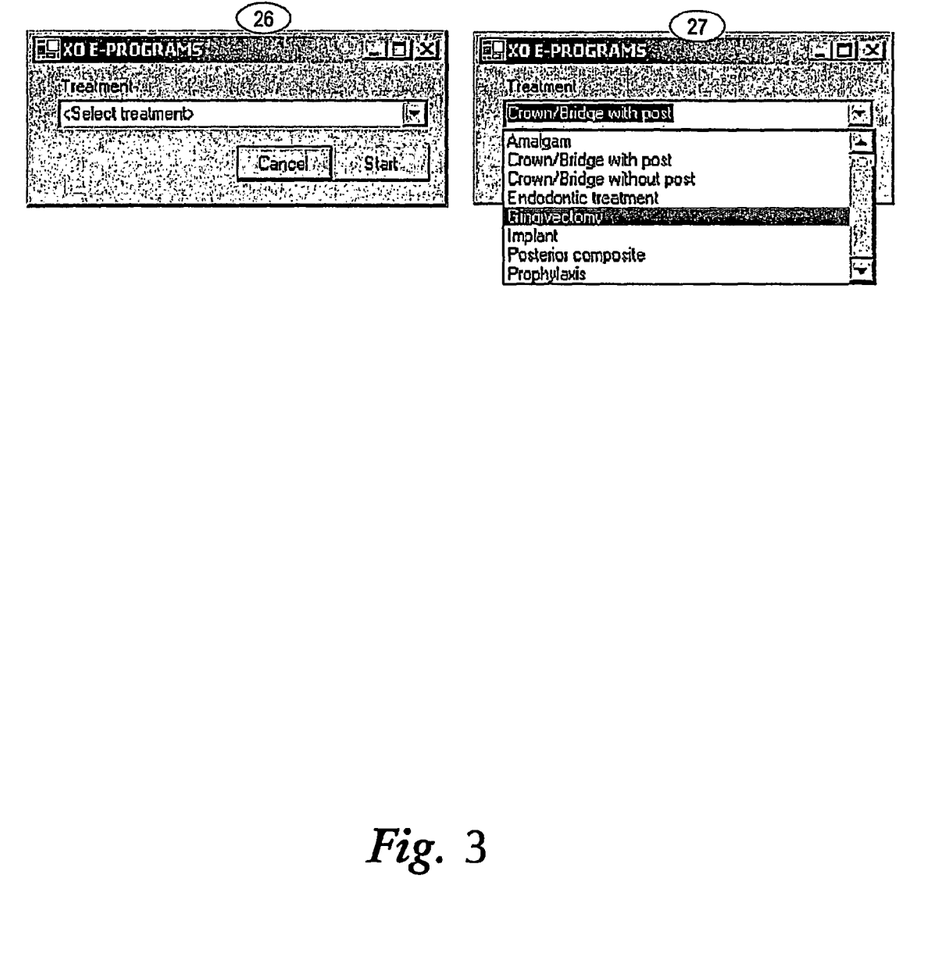
FIGS. 3 and 4 are screen image representations of examples of protocols and treatments for use in the information and control system of the invention.
Figure 4:
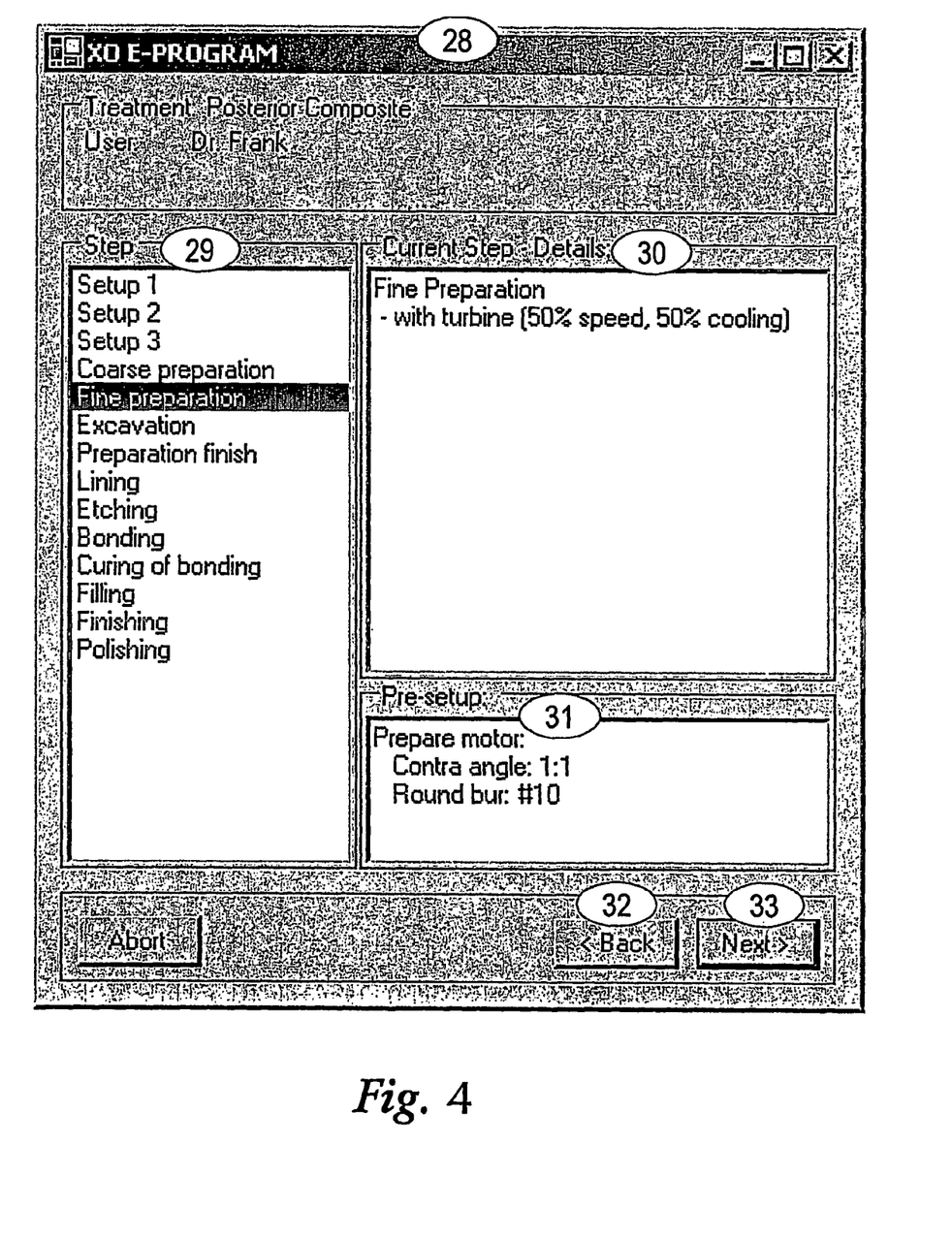

In FIGS. 3 and 4, examples of a protocol and a treatment, respectively, for use in the information and control system of the invention are illustrated by way of screen image representations in the conventional WINDOWS® format.

Thus, for the protocol in FIG. 3, a selection window is illustrated in its initial state 26 before any treatment selection has been made, as well as in its selection state 27, which is obtained by a mouse click on the pull-down arrow button to the right of the "select treatment" indication in the initial configuration. In the illustrated example of a selection configuration 27, a range of eight selectable treatments is listed, from which a specific treatment can be selected by a mouse click operation or operation of up/down arrows and entry keys on the computer keyboard.

Once a specific treatment has been selected, the range of selectable treatments will disappear from the treatment selection window and by operation of the "start" button in the window, which has become active by the selection, e.g. by a mouse click or operation of the keyboard entry key, the treatment window 28 illustrated in FIG. 4 will appear on the computer's display screen.

In the illustrated example, the treatment window includes three separate fields 29 to 31, of which the field 29 contains a listing of separate steps or actions to be performed in preparation for and in the course of the selected treatment, whereas the second field 30 is used for the display of important details of an individual step or action currently highlighted by mouse pointing or the up/down arrow keys on the computer keyboard, and the third field 31 may be a pre-set-up field that may be used for indication of preparatory sub-actions which would need to be taken in preparation for one of the following sequential actions listed in the field 29. This particularly feature may e.g. make it possible for the dental nurse to work ahead of the dentist by making preparations for subsequent steps or actions of the selected treatment.

The first steps or actions listed in the field 29 may involve setting-up for preparing the selected treatment, such as finding and preparing required filling materials and other consumables, finding and preparing dental instruments, including hand instruments 47, as well as instruments powered by the dental unit as shown in FIG. 2, which are controlled by the dental unit, the preparation of such instruments involving e.g. selection of required contra angles for the head part of the selected instrument as well as appropriate drills.

In each step or action listed in the treatment operation parameters such as e.g. rotational speed of a drilling instrument, amount and composition of a water-air spray coolant or torque may be set up and, as will become apparent in the following, parameter values set up by means of the actions and communicated to the dental unit 1 may take priority over adjustments previously made by means of the microprocessor forming part of the dental unit.

The selection of individual steps or actions listed in the field 29 may be performed by either the dentist or the dental nurse by inputting appropriate commands to the computer configuration as will be further detailed below. Typically the dentist or dental nurse will proceed sequentially through the listed steps or actions, but obviously each listed step or action may be selected individually. A NEXT button 33 and a BACK button 32 are provided for navigating between the treatments.

It will be possible as well to move either forwards or backwards in the sequence of listed steps or actions, and if a treatment is interrupted for any reason, the protocol may be interrupted accordingly such that the treatment may be resumed at any later occasion. Button(s) for this purpose are not shown in FIG. 4.

Figure 5:
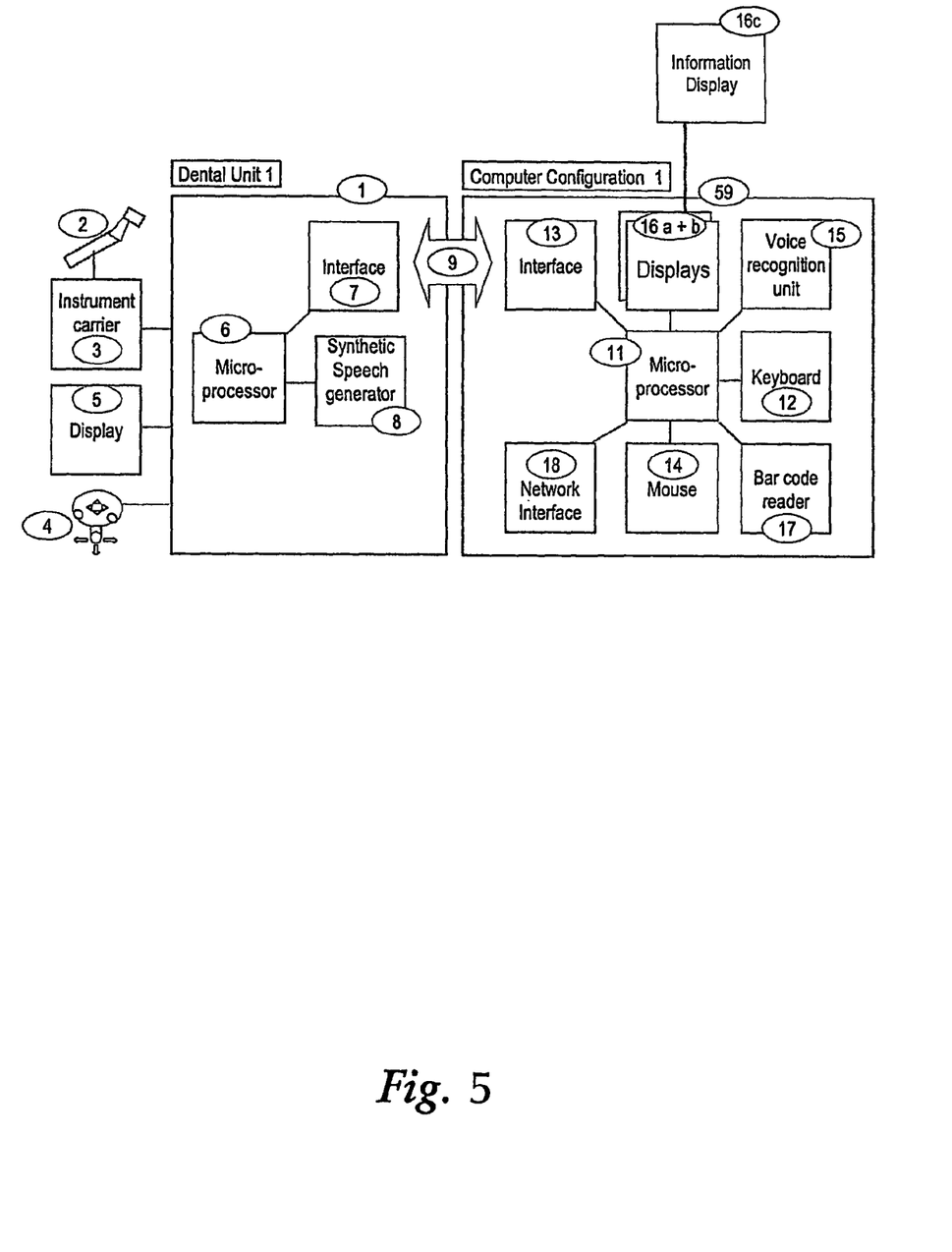
FIG. 5 is an organisation plan of a dental environment as illustrated in FIG. 1.

In accordance with the invention, and as illustrated by the exemplified organisation plan in FIG. 5, the computer configuration as illustrated in FIG. 1 is operatively connected or connectible with the protocol display means including display screens 16a to 16c in FIG. 1 as well as with protocol control means that are operable by the dentist or the dental nurse for inputting commands to the computer for selection of treatment and actions listed in the treatment protocols, e.g. as illustrated in FIGS. 3 and 4.

The organisation plan in FIG. 5 depicts the structure of the computer configuration 59 and its interconnection with the dental unit 1 and the interconnection of the latter with the instrument carrier 3 with its instruments 2 and display 5, and the foot-operated control device 4.

As mentioned above, the computer configuration 59 comprises traditional components 11-14, 16a-b, and 18, all well known per se from personal computers, plus optional interface 13 for communication with the dental unit 1 via a data communication connection 9 such as a cable, voice recognition unit 15 and bar code reader 17.

When using the voice recognition unit for inputting commands to the computer configuration 59, a microphone 62 will be mounted at or near the dentist's working position 55, or mounted on e.g. the clothes of the dentist.

The communication between the dental unit 1 and the computer configuration 59 provided by the present invention is made through interfaces 13, 7 in the computer configuration and the dental unit 1, respectively. In the illustrated example, the dental unit 1 comprises in addition to the microprocessor 6 and the interface 7, a synthetic speech generator 8, which may be included to provide a further means of communication of information to the dentist and the dental nurse, as well as to the patient.

The dental unit 1 is communicating with the instrument carrier 3 with dental instruments 2, the foot-operated control device 4, and the instrument carrier display 5 displaying instrument parameters.

Figure 6:
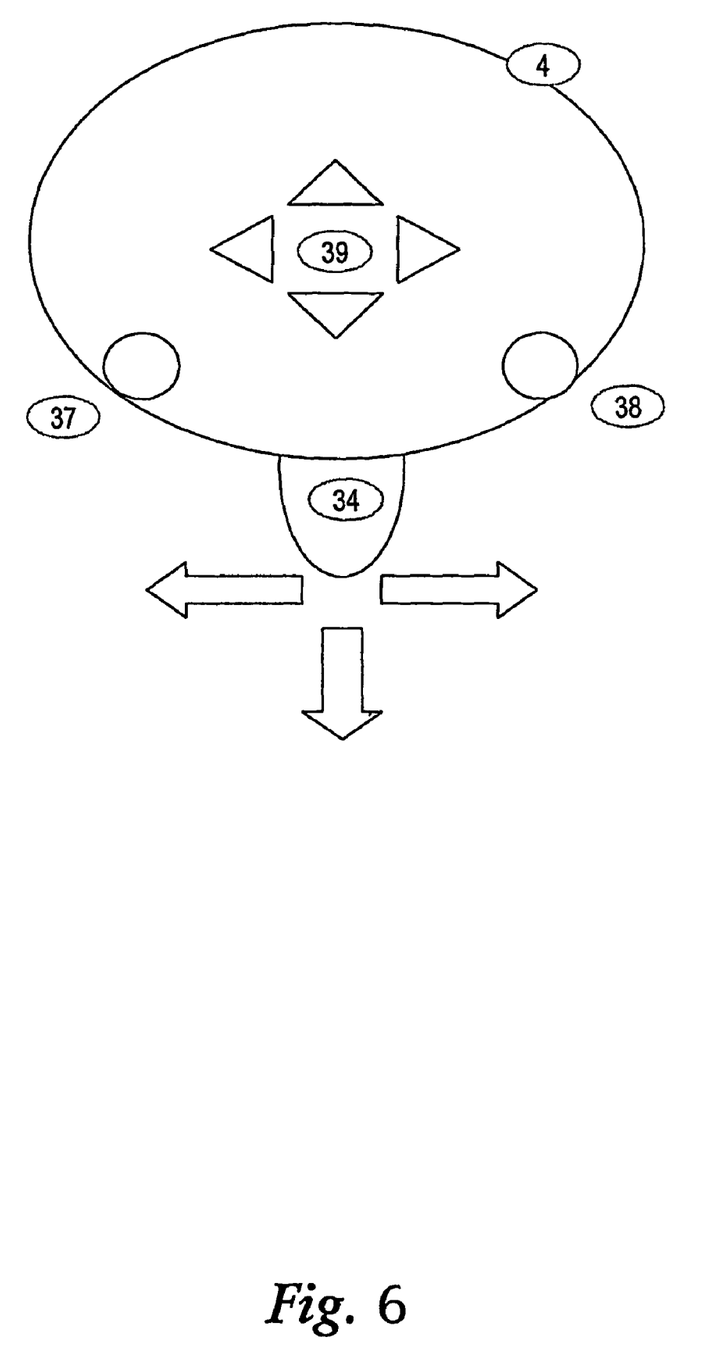
FIG. 6 is a top view of a foot-operated control device for integrated control of the dental unit and the information and control system.

FIG. 6 illustrates an embodiment of a foot-operated control device 4. According to this embodiment, a dental instrument is controlled in a conventional manner via the foot-operated control device 4 as long as the instrument 2 is kept lifted from the instrument carrier 3. Such normal operation is conveniently performed using a main control member 34, preferably embodied as a switch member or an arm situated on the side of the foot-operated control device.

Auxiliary control members 37, 38 and 39 on the foot-operated control device are e.g. usable for changing parameters of a dental unit instrument presently in use.

Figure 7:
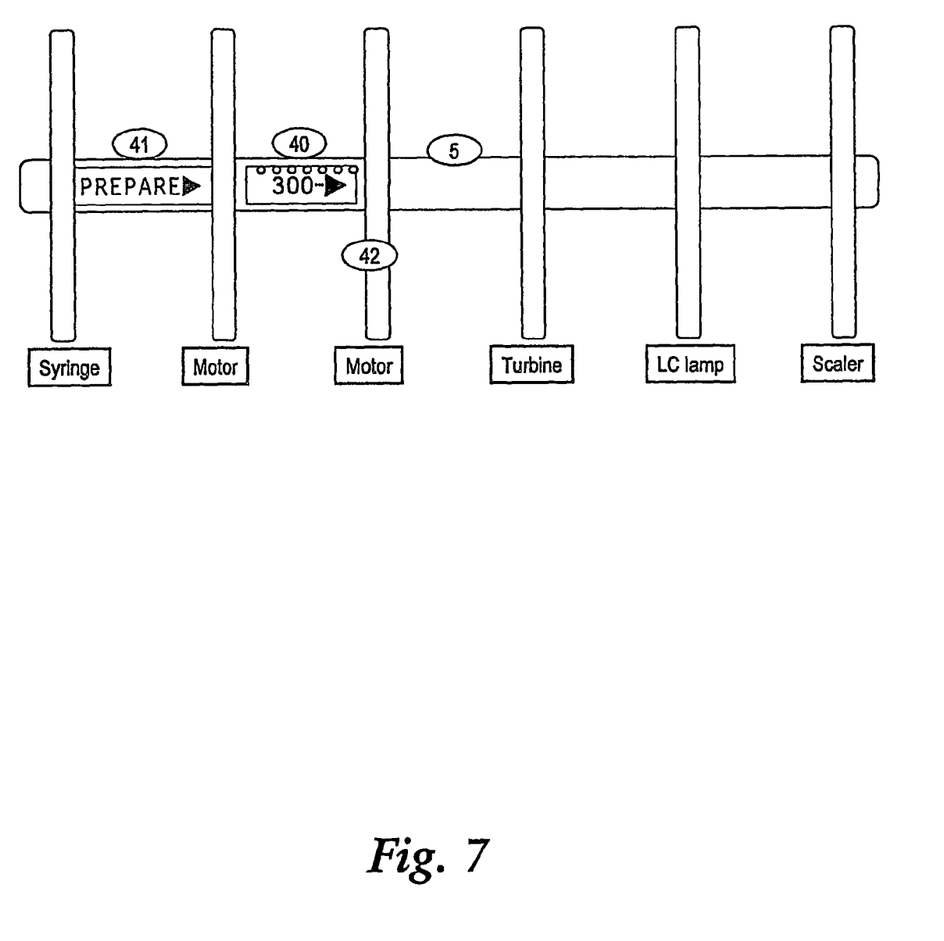
FIG. 7 is a modified representation of another example of an instrument carrying means with integrated information display as shown in FIG. 2.

When parameters are being changed this way or, in more general, via the computer configuration, the instrument carrier display 5 may display the parameter in question, as it is shown in FIG. 7, where the rotational speed of a motor 42 in position No. 3 is displayed as "300" at 40.

When no instrument is lifted from the instrument carrier, the controls associated with the control of the instruments 2 are converted to functions associated with the input of commands to the information and control system of the invention, e.g. as per the following description, which is given by way of example:

Activation of the main control member 34 to the right (FIG. 6) selects a cell on the computer display to the right of the present cell, and activating said control to the left selects the cell to the left. Moving the main control member 34 downwards activates a selected cell.

Further, the control members 37-39 may be given the functionality of a point-and-click device or "mouse", a joystick 39 positioning the cursor on the computer screen, and the controls 37-38 functioning as left and right mouse buttons, respectively.

If the dental nurse is preparing instruments for use in a subsequent step of the treatment as explained above with reference to FIG. 4 and pos. 31, the instrument carrier display 5 may highlight an instrument to be prepared, as shown at 41 in FIG. 7.

As mentioned in the introductory part of the present description, the information and control system of the invention is preferably provided with extensive logging capabilities.

These provide for vast improvements in the possibilities of the dentist for documenting and proving treatments performed on patients. This advantage of the invention will assist the dentist to keep a high degree of accuracy, detail and reliability in the patient's records, which is very important, as most dentists are subjected to specific medical responsibility.

As record-keeping is however a time-consuming task, relieving the dentist of this task, or at least supporting the record-keeping to a substantial degree, will be an important improvement of the dentist's working environment as well.

Figure 8:
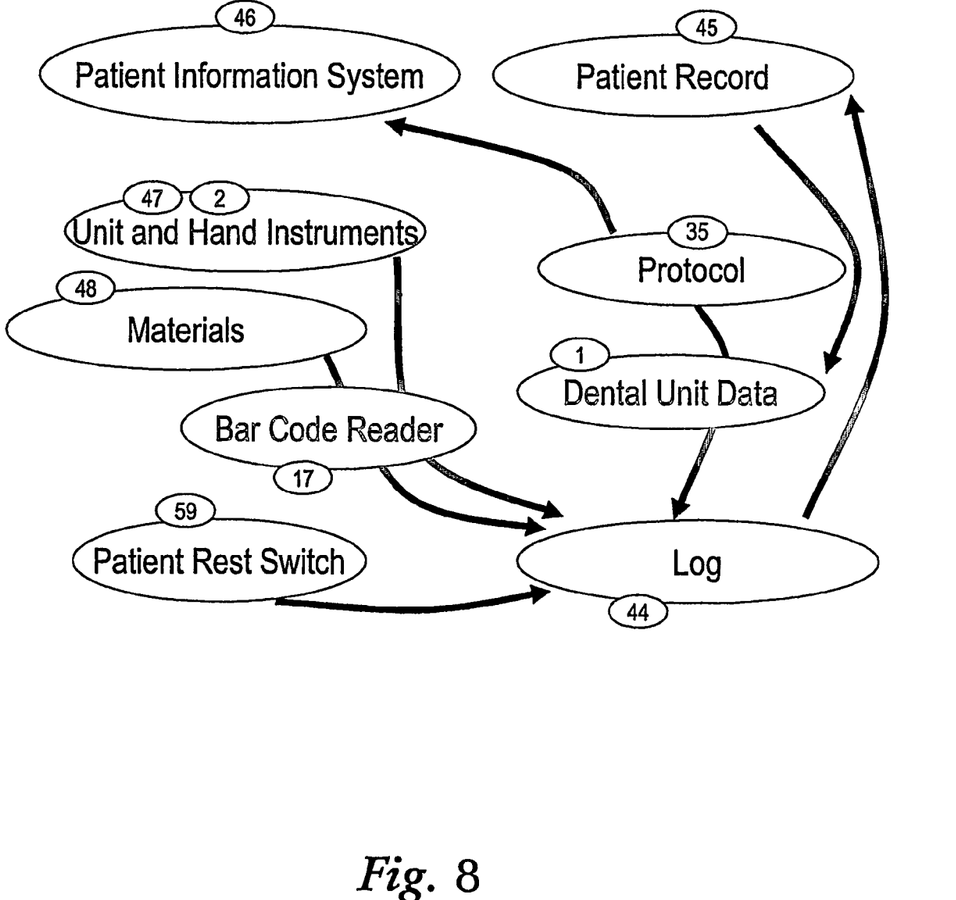
FIG. 8 is a flow diagram representation of patient information and logging features of the information and control system.

According to the invention, all data related to the treatment of the patient are preferably logged. The logging capabilities of a preferred embodiment of the information and control system of the invention are illustrated in FIG. 8. The log in the computer configuration 1 or a server 20 (cf. below) is generally designated by 44.

Logging of a patient entering the rest, and leaving it after treatment may be accomplished by providing the patient's rest 43 with a sensor sensing the load on the rest, such as a cushioning switch 59 (not shown) sensing the weight of the patient.

From the protocol, data from the treatment window 28 (FIG. 4) are logged, together with instrument parameter data from the dental unit 1. From the protocol (35), selected and/or edited data are transferred to a patient information system 46 for display on the patient's display 16c (FIG. 1).

Any particular instrument setting, which may be required for a particular patient, may be transferred from a patient record 45 stored in the computer configuration or on a network (please cf. below) to the dental unit 1, where the relevant instrument parameters are set accordingly. Provisions are preferably made for drawing the attention of the dentist to such extraordinary settings.

Particular instruments used, both instruments 2 from the instrument carrier 3 and hand instruments 47, may be registered via a bar code reader 17, and their use thus logged by the system. Substances, consumables or ancillary materials 48 may be registered the same way, and their use logged accordingly.

As known per se, the log will preferably be provided with facilities disabling or impeding editing or deleting the logged data, in order to prevent tampering with logged data and thus increase the credibility of the log.

Figure 9:
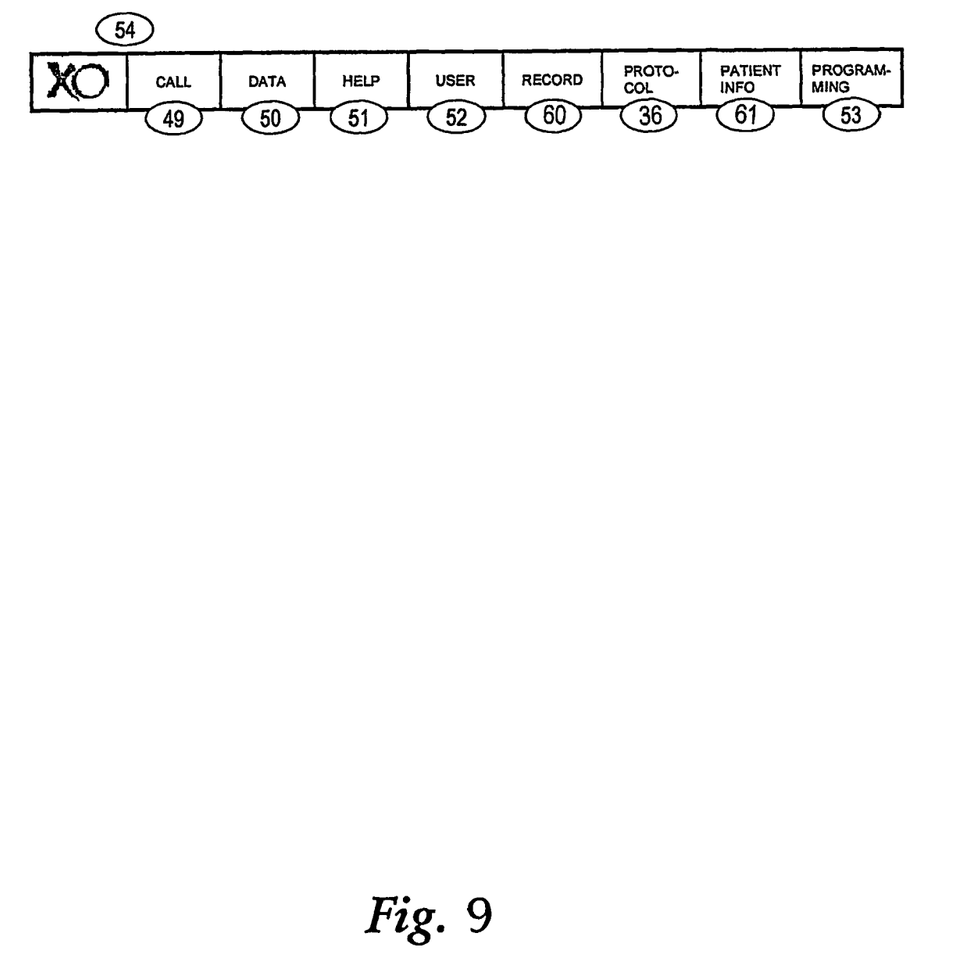
FIG. 9 shows an example of a menu bar used for menu selection in a further development of the information and control system.

According to the invention, a menu bar 54 is displayed in one or more of the screen images on the computer displays 16*a*, 16*b*; the menu bar is shown in FIG. 9. In the embodiment example in FIG. 9, the menu bar has eight buttons, of which only one may be selected at any one time.

A button may be selected by means of a single click with the mouse 14; from the keyboard 12; via the voice recognition unit 15; or via the foot-operated control device 4.

A button 49 CALL is provided for summoning the dental nurse.

When the button 50 DATA is activated, a complete list of the instruments on the dental unit instrument carrier 3 data is shown on one or more of the displays 16*a-b*, enabling the dental nurse and the dentist to see exactly which parameters are selected at any one time.

Activating the button 51 HELP causes a context sensitive user manual to be shown on one or more of the displays 16*a-b*. Depending on the actual state of the dental unit 1, the functioning of relevant input devices—in particular the foot-operated control device 4—is indicated.

With button 52 USER, the dentist may choose his own personal programmes and settings of the dental unit, as well as his individual treatment protocols (35).

Access to the patient record system is obtained via the button 60 RECORD.

In the same way, access to the protocols and the patient information system is achieved via the buttons 28 PROTOCOL and 61 PATIENT INFO.

Figure 10:
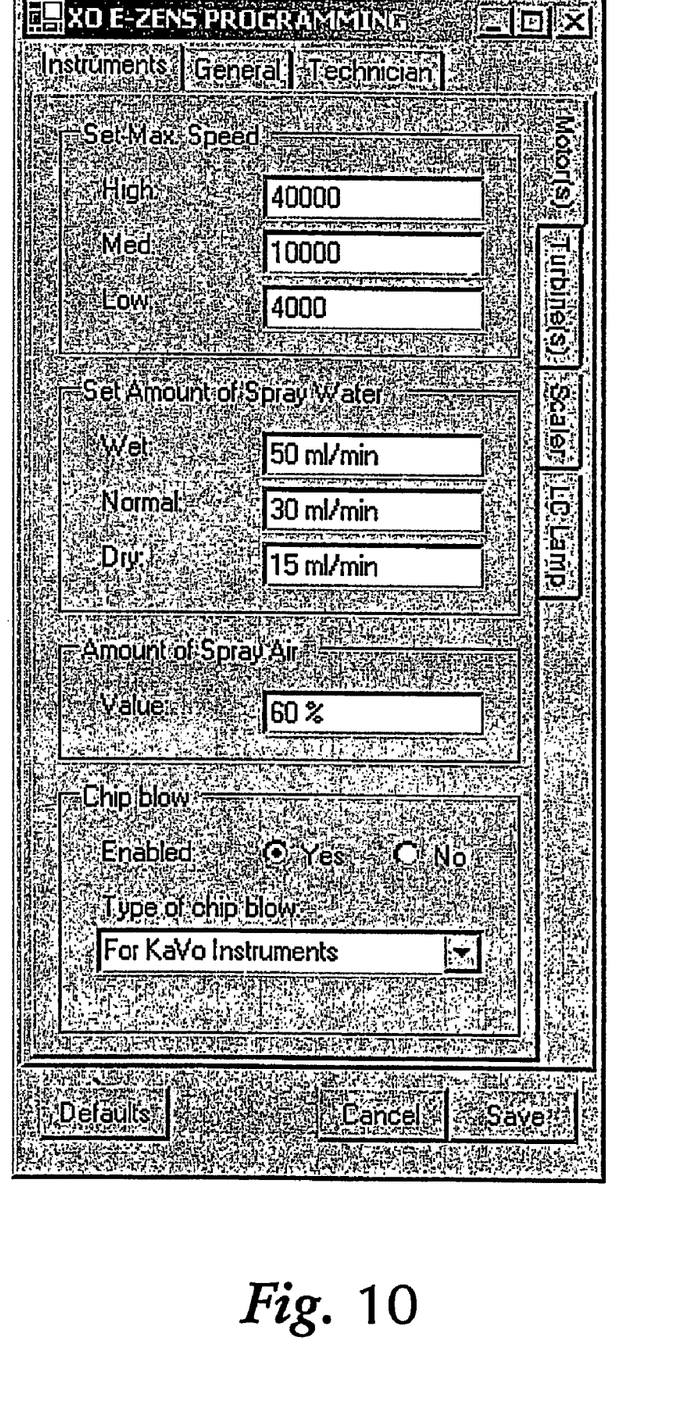
FIG. 10 is a screen image representation of parameter adjustment features of the dental unit.

Programming of the microprocessor 6 of the dental unit 1, which corresponds to the basic functioning of the dental unit 1 when no protocols 28 are active, may be done by activating the button 53 PROGRAMMING of the menu bar 54, following which a programming menu as shown in FIG. 10 will be accessible, and will be displayed on one or more of the displays 16*a-b*.

In the embodiment example in FIG. 10, such a programming window is illustrated, as shown on the display(s) 16*a-b* of the computer configuration of the invention. By means of lateral tabs at the top of the window, programming of the parameters of instruments has been selected, and by means of the vertical tabs to the right in the window, programming of the parameters of the motor(s) has been selected.

In the selected window, the user now has the opportunity of presetting or programming three maximum speed values; three values of spray water amount, one value of spray air, and enabling and type of chip blow. Default values may be selected by means of the lower left button, and the values chosen may be saved by use of the lower right button.

Figure 11:
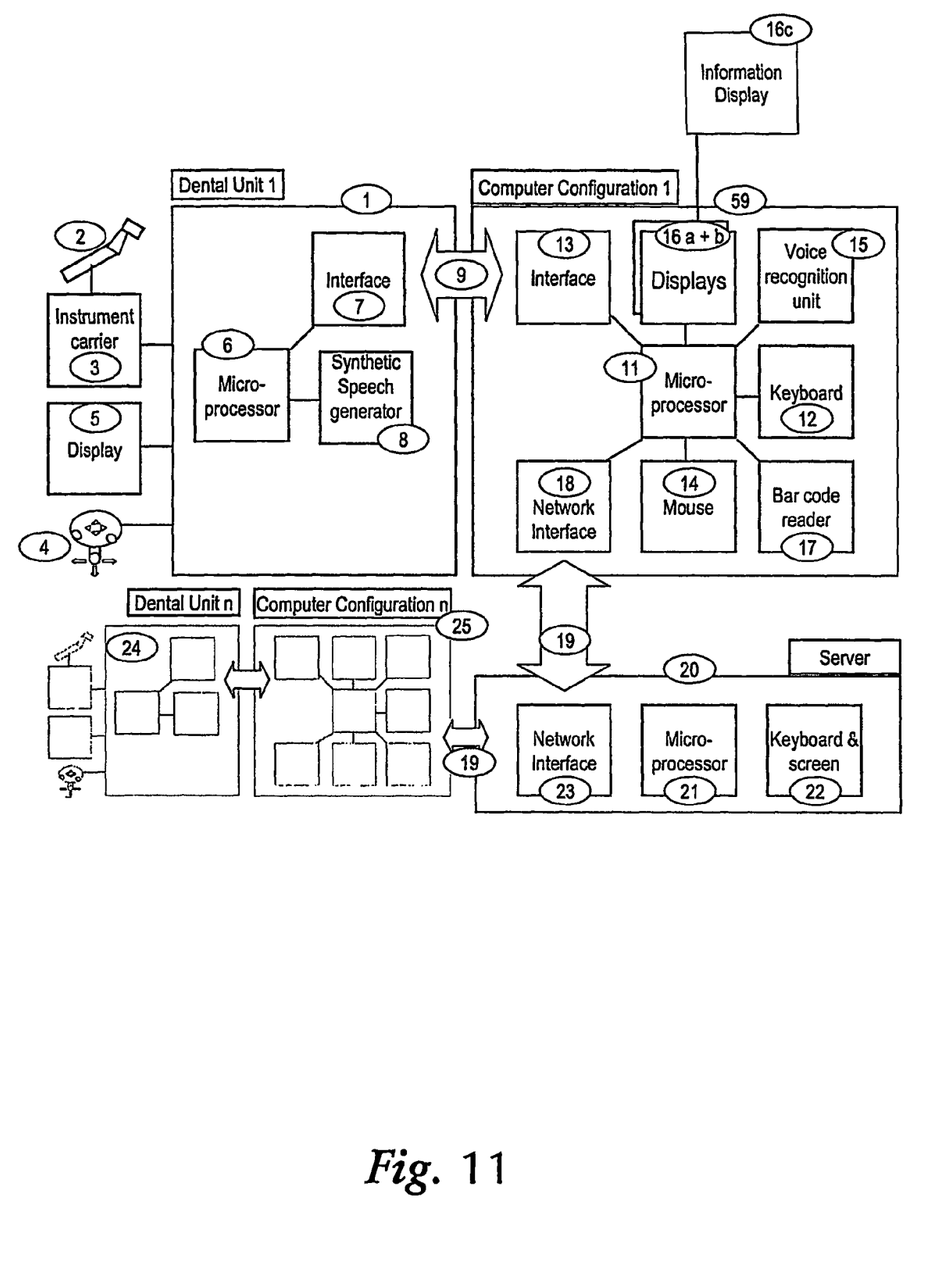
FIG. 11 is an organisation plan of a multi-user development of an information and control system according to the invention.

FIG. 11 illustrates interconnection of a number of computer configurations of the invention into a common network for a dental practice comprising a number of dentists. The dental unit No. 1 (1) and the computer configuration No. 1 (59) represent the equipment related to one dentist, or one treatment facility in a dental clinic. The dental unit No. n (24) and the computer configuration No. n (25) represent similar installations at the premises or the clinic of another dentist, or in another treatment facility of a dental clinic in question.

A central server 20 may be provided for overall network administration and central data storage in a way known per se. The connection(s) between two computer configurations 59, 25 or between each computer configuration and the server, respectively, is shown at 19. The server 20 is a more or less specialised computer comprising a microprocessor 21, possibly keyboard and display 22, and necessary network interfaces 23.

Even if the WINDOWS® computer display format is referred to in connection with FIGS. 3-4, the information and control system of the invention may obviously be implemented using any operating system or computer topology.

REFERENCE NUMBERS

1 dental unit No. 1
2 powered instrument
2*a-f* do.
3 instrument carrier
4 foot-operated control device
5 instrument carrier display
6 microprocessor
7 dental unit interface
8 speech generator
9 data connection
10 computer processing station
11 microprocessor
12 keyboard
13 computer interface
14 computer mouse
15 voice recognition unit
16*a-b* computer displays
16*c* patient's information display
17 bar code reader
18 network interface
19 network connections
20 network server
21 microprocessor
22 server keyboard and display
23 server network interface
24 dental unit No. n
25 computer configuration No. n
26 select-treatment window
27 do.
28 treatment window
29 list-of-steps field
30 description field
31 pre-set-ups field
32 BACK button
33 NEXT button
34 main control member
35 protocol
36 PROTOCOL button
37 control member
38 do.
39 foot-operated joystick
40 display of a parameter
41 display of PREPARE
42 instrument being programmed
43 patient's rest
44 log
45 patient's record
46 patient information system
47 hand instruments
48 materials
49 CALL menu bar button
50 DATA menu bar button
51 HELP menu bar button
52 USER menu bar button
53 PROGRAMMING menu bar button
54 menu bar
55 dentist's working position 56 dental nurse's working position
57 hand instrument cabinet
58 powered instrument in use
59 cushioning switch in patient's rest
60 RECORD button
61 PATIENT INFO button
62 microphone

The invention claimed is:

1. An information and control system for use in a dental environment, said environment incorporating a dental unit including a number of individually selectable dental instruments, at least one instrument control member for controlling the operation of a selected instrument, a patients rest and working positions for a dentist and a dental nurse in operative relationship to said dental unit and said patient's rest, said information and control system comprising:
   computer means storing sequences of treatments for dental conditions; and
   display means for display of a sequence of treatments for a dental condition,
   said computer means storing at least one treatment protocol listing a range of selectable dental treatments, and for each listed treatment a range of sequential steps or actions to be performed in preparation and conduct of the treatment, said display means comprising protocol display means operatively connected with the computer means for display of said treatments and steps or actions to the dentist and/or the dental nurse,
   the information and control system further comprising protocol control means for operation by the dentist and/or the dental nurse for inputting commands to said computer means for selection of treatments, steps and/or actions listed in said protocols.

2. An information and control system as claimed in claim 1, wherein an information display means is disposed at instrument carrying means at said dental unit, for display of information transferred from said computer means and related to the use of a dental instrument in said dental unit.

3. An information and control system as claimed in claim 1, wherein:
   said dental unit comprises micro processor means for controlling operational parameters for a selected instrument,
   said treatment protocol comprising at least one treatment including at least one step or action involving the use of at least one dental instrument in the dental unit, for which a value of at least one operational parameter is stored in said computer means, and
   said computer means being operatively connected or connectible with said microprocessor means in the dental unit for communication of said parameter value to said microprocessor means and adjustment of said operational parameter to said stored value upon selection of said dental instrument.

4. An information and control system as claimed in claim 3, wherein values of operational parameters are programmable via said computer means.

5. An information and control system as claimed in claim 3, wherein a parameter display means is disposed at instrument carrying means at said dental unit, for display of said parameter value when communicated to said microprocessor means.

6. An information and control system as claimed in claim 5, wherein said information display means and said parameter display means are constituted by one and the same display.

7. An information and control system as claimed in claim 1, wherein said protocol control means comprises any of a keyboard, a point and click device, a voice recognition device and a separate protocol control member disposed in relationship with said instrument control member.

8. An information and control system as claimed in claim 7, wherein said instrument control member and said separate protocol control member are integrated in a single foot-operated control device.

9. An information and control system as claimed in claim 8, wherein the functioning of specific controls on said foot-operated control device are programmable via the computer means.

10. An information and control system as claimed in any one of claims 1-9, wherein said protocol display means comprises a patient's display disposed within a field of vision for a patient resting in said patient's rest.

11. An information and control system as claimed in claim 10, comprising provisions for displaying real time data on said patient's display related to the treatment, step or action presently performed.

12. An information and control system as claimed in claim 1, wherein said patient's rest is equipped with means such as a cushioning switch for sensing the presence of a patient in the rest.

13. An information and control system as claimed in claim 1, wherein said computer means comprises logging means for storing information, in particular logging information related to any selected treatment and/or any of said sequential actions performed in the course of said treatment.

14. An information and control system as claimed in claim 13, wherein said logging means are adapted to logging the presence of a patient in the patient's rest; the name of the dentist and possible the dental nurse; and preferably the name of the patient.

15. An information and control system as claimed in claim 13, wherein said logging means are adapted to logging the treatments performed, including data such as version number identifying a particular treatment, or possible deviations made from treatments.

16. An information and control system as claimed in claim 13, wherein said logging means are adapted to logging time data related to the treatments performed, such as point of time for start of a treatment, a step or an action, and the duration or the point of time of completion of same.

17. An information and control system as claimed in claim 16, wherein said logging means are adapted to logging time data related to the dental instruments used, such as point of time for start of the use of each instrument and the duration of same, and accumulated periods of use for each instrument.

18. An information and control system as claimed in claim 13, wherein said logging means are adapted to logging points of time for the patient entering and leaving, respectively, the patient's rest, as registered by said presence sensing means.

19. An information and control system as claimed in claim 13, wherein said logging means are adapted to logging environmental data such as water quality, temperature and/or moisture of air.

20. An information and control system as claimed in claim 13, wherein said logging means are adapted to logging bar code data, preferably from bar codes present on items presented to a bar code reader connected to said computer means during a treatment.

21. An information and control system as claimed in claim 13, characterised by the provision of means preventing deletion of logged data.

22. An information system as claimed in claim 1, wherein said computer means forms part of a multi-user network including a server computer connected with computer means associated with a number of dental units, whereby said treatment protocols are stored in said server computer for shared use by all of said computer means and the dental units associated therewith.

23. An information and control system as claimed in claim 22, wherein said server computer is adapted for storing of user-defined treatment protocols in addition to said shared protocols.

24. An information and control system as claimed in claim 1, wherein the computer means associated with a dental unit and/or said server computer is adapted for storing a patient's register for patients of a dental practice, said register containing records of treatments and actions performed on each patient therein.

25. An information and control system as claimed in claim 24, wherein, for a specific patient's record, said computer means is adapted for modification of steps or actions listed in said treatment protocol for any of said selectable treatments on the basis of information on prior treatments recorded in the patient's record.

26. An information and control system as claimed in claim 24, wherein, for a specific patient's record, said computer means is adapted for storing information related to the patient such as position adjustment data for the patient's rest.

* * * * *